United States Patent
Benson et al.

(10) Patent No.: US 11,278,238 B2
(45) Date of Patent: Mar. 22, 2022

(54) WEARABLE SENSOR DEVICE AND ANALYSIS PLATFORM FOR OBJECTIVE OUTCOME ASSESSMENT IN SPINAL DISEASES

(71) Applicant: Warsaw Orthopedic, Inc., Warsaw, IN (US)

(72) Inventors: Nicholas M. Benson, Collierville, TN (US); Richard L. Brown, Mesa, AZ (US); Newton H. Metcalf, Memphis, TN (US); Clark B. Norgaard, Phoenix, AZ (US); Steven D. Glassman, Louisville, KY (US); Shane Burch, San Anselmo, CA (US); Domagoj Coric, Charlotte, NC (US); Robert A. Fields, Memphis, TN (US); Seth Georgion, San Diego, CA (US); Wing Au, Saratoga, CA (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 378 days.

(21) Appl. No.: 16/132,094

(22) Filed: Sep. 14, 2018

(65) Prior Publication Data

US 2020/0085366 A1    Mar. 19, 2020

(51) Int. Cl.
*A61B 5/11* (2006.01)
*A61B 5/00* (2006.01)
(Continued)

(52) U.S. Cl.
CPC .......... *A61B 5/4566* (2013.01); *A61B 5/0002* (2013.01); *A61B 5/02055* (2013.01);
(Continued)

(58) Field of Classification Search
CPC ... A61B 5/4566; A61B 5/6823; A61B 5/7267; A61B 5/0402; A61B 5/02055;
(Continued)

(56) References Cited

U.S. PATENT DOCUMENTS

| 7,918,887 B2 | 5/2011 | Roche |
| 8,372,153 B2 | 2/2013 | Roche |

(Continued)

FOREIGN PATENT DOCUMENTS

| JP | 2015532841 A | 11/2015 |
| KR | 10-1851690 B1 | 4/2018 |
| WO | 2013109762 A1 | 7/2013 |

OTHER PUBLICATIONS

A. S. A. Sukor, et al, "Activity recognition using accelerometer sensor and machine learning classifiers," 2018 IEEE 14th International Colloquium on Signal Processing & its Applications (CSPA), Batu Feringghi, 2018, pp. 233-238, doi: 10.1109/CSPA.2018.8368718. (Year: 2018).*

(Continued)

*Primary Examiner* — David J. McCrosky
(74) *Attorney, Agent, or Firm* — Fox Rothschild LLP (57) ABSTRACT

A system for assessing a spinal disorder includes a wearable electronic device having one or more sensors and an assessment system. The wearable electronic device is configured to be positioned on a portion of a lower back of a wearer, and the one or more sensors are configured to obtain patient data associated with the wearer. The system receives patient data from the one or more sensors, where the patient data includes movement data associated with movement of the lower back of the wearer, classifies the movement data into an initial grouping, further classifies the at least a portion of the movement data into one of the plurality of activity (Continued)

categories, generate a score corresponding to the at least a portion of the movement data based on the activity category to which the movement data is classified, and cause the score to be displayed via a client electronic device.

18 Claims, 4 Drawing Sheets (51) Int. Cl.
| | |
|---|---|
| *G16H 40/63* | (2018.01) |
| *G16H 50/20* | (2018.01) |
| *G06N 5/02* | (2006.01) |
| *A61B 5/0205* | (2006.01) |
| *A61B 5/18* | (2006.01) |
| *G06F 1/16* | (2006.01) |
| *A61B 5/318* | (2021.01) |
| *A61B 5/024* | (2006.01) |

(52) U.S. Cl.
CPC .............. *A61B 5/1123* (2013.01); *A61B 5/18* (2013.01); *A61B 5/318* (2021.01); *A61B 5/4809* (2013.01); *A61B 5/6823* (2013.01); *A61B 5/7267* (2013.01); *A61B 5/742* (2013.01); *G06F 1/163* (2013.01); *G06N 5/02* (2013.01); *G16H 40/63* (2018.01); *G16H 50/20* (2018.01); *A61B 5/02416* (2013.01); *A61B 2560/0257* (2013.01); *A61B 2562/0204* (2013.01); *A61B 2562/0219* (2013.01); *A61B 2562/0271* (2013.01)

(58) Field of Classification Search
CPC ..... A61B 5/1123; A61B 5/4809; A61B 5/742; A61B 5/0002; A61B 5/18; A61B 5/02416; A61B 2562/0219; A61B 2562/0271; A61B 2562/0204; A61B 2560/0257; A61B 5/6832; A61B 2560/0412; A61B 5/7264; A61B 5/7282; A61B 5/4561; A61B 5/4571; A61B 5/4519; A61B 5/4538; A61B 5/1114; A61B 5/1116; A61B 5/1118; A61B 5/112–1128; A61B 2562/04; A61B 2562/043; A61B 2562/046; A61B 2562/06; A61B 2562/063; A61B 2562/066; G16H 40/63; G16H 50/20; G16H 50/30; G16H 50/70; G06N 5/02; G06F 1/163; G06F 1/1694
USPC .................................................. 600/300, 301
See application file for complete search history.

(56) References Cited

U.S. PATENT DOCUMENTS

| | | | |
|---|---|---|---|
| 8,444,654 B2 | 5/2013 | Roche | |
| 8,449,556 B2 | 5/2013 | Roche | |
| 2009/0298650 A1 | 12/2009 | Kutliroff | |
| 2012/0000300 A1* | 1/2012 | Sunagawa | A61B 5/1122 73/865.4 |
| 2013/0096396 A1* | 4/2013 | Riedel | A61B 5/14546 600/301 |
| 2013/0253334 A1* | 9/2013 | Al-Ali | A61B 5/0024 600/300 |
| 2016/0270927 A1 | 9/2016 | Zeller et al. | |
| 2016/0331415 A1 | 11/2016 | Serhan et al. | |
| 2017/0007420 A1 | 1/2017 | Stevenson et al. | |

OTHER PUBLICATIONS

Loske, Stefan, et al. "Decompression surgery improves gait quality in patients with symptomatic lumbar spinal stenosis." The Spine Journal 18.12 (2018): 2195-2204. (Year: 2018).*
Demonceau, Marie, et al. "Contribution of a trunk accelerometer system to the characterization of gait in patients with mild-to-moderate Parkinson's disease." IEEE journal of biomedical and health informatics 19.6 (2015): 1803-1808. (Year: 2015).*
Ahmadi, Amin, et al. "Automatic activity classification and movement assessment during a sports training session using wearable inertial sensors." 2014 11th International Conference on Wearable and Implantable Body Sensor Networks. IEEE, 2014. (Year: 2014).*
Liu, Ye, et al. "From action to activity: sensor-based activity recognition." Neurocomputing 181 (2016): 108-115. (Year: 2016).*
Trost, et al. "Conducting accelerometer-based activity assessments in field-based research." Medicine & Science in Sports & Exercise 37.11 (2005): S531-S543. (Year: 2005).*
Conway, Justin, Christy C. Tomkins, and Andrew J. Haig. "Walking assessment in people with lumbar spinal stenosis: capacity, performance, and self-report measures." The Spine Journal 11.9 (2011): 816-823. (Year: 2011).*
Rodríguez-Martín, et al. "A wearable inertial measurement unit for long-term monitoring in the dependency care area." Sensors 13.10 (2013): 14079-14104. (Year: 2016).*
International Search Report for corresponding application No. PCT/US2019/050717 dated Sep. 12, 2019.

* cited by examiner

WEARABLE SENSOR DEVICE AND ANALYSIS PLATFORM FOR OBJECTIVE OUTCOME ASSESSMENT IN SPINAL DISEASES

The present disclosure generally relates to a wearable spine sensor or multi-sensor device that utilizes artificial intelligence to measure and categorize patient activities, and provide multiple stakeholders such as, for example, clinicians, patients, insurers and employers, with objective information pertaining to a patient's spinal condition.

BACKGROUND

A patient's spinal condition is generally evaluated using a combination of patient feedback, imaging technologies and clinician evaluations. For example, many clinicians use the Oswestry Disability Index (ODI) to evaluate a patient's functional disability resulting from back pain. ODI includes questions asking a patient to evaluate the contribution of low back-related symptoms to his or her pain level with respect to certain activities such as sitting, standing, sleeping and traveling.

However, data collected via these methods can be fallible, and in some cases misleading as to the patient's true condition. For example, a patient's responses to ODI questions (or other patient-provided descriptions or characterizations of the patient's pain level) may be inaccurate or incomplete. In addition, the questions posed by the ODI may not adequately describe the nature of the patient's condition.

Since data pertaining to a patient's movement can contain valuable information about the health of the patient's neurological function and musculoskeletal health, it is desirable to obtain this information in an objective rather than subjective manner. Additionally, the ODI and similar clinical measurement tools are burdensome to incorporate into everyday clinical practice, often requiring the addition of a full-time employee to dispense, tabulate and manage.

SUMMARY

In an embodiment, a system for assessing a spinal disorder includes a wearable electronic device having one or more sensors. The wearable electronic device is configured to be positioned on a portion of a lower back of a wearer, and the one or more sensors are configured to obtain patient data associated with the wearer. The system includes an assessment system having a computing device, and a computer-readable storage medium having one or more programming instructions. The programming instructions, when executed, cause the computing device to receive patient data from the one or more sensors over a period of time, where the patient data comprises movement data associated with movement of the lower back of the wearer, classify at least a portion of the movement data into an initial grouping, where the initial grouping is associated with a plurality of activity categories that correspond to different types of movement, further classify the at least a portion of the movement data into one of the plurality of activity categories, generate a score corresponding to the at least a portion of the movement data based on the activity category to which the movement data is classified, and cause the score to be displayed via a client electronic device.

The one or more sensors may include one or more of the following: an inertial measurement unit; an electrocardiogram sensor; an altimeter; a barometer; a photoplethysmogram; a thermometer; or a microphone. The patient data may include measurements related to one or more of the following: electrical activity information; sound information; or temperature information.

In an embodiment, the system may classify at least a portion of the movement data into an initial grouping by comparing one or more parameter values of the movement data to one or more parameters associated with one or more possible initial groupings.

The system may classify the at least a portion of the movement data into one of the plurality of activity categories by comparing the at least a portion of the movement data to a trained data set to determine a probability that the at least a portion of the movement data corresponds to a pattern associated with one of the plurality of activity categories. The system may use the at least a portion of the movement data to train or reinforce the trained data set as to movement specific to the wearer.

In an embodiment, the activity categories may include one or more of the following: sleeping; driving; sitting; standing; or walking.

In various embodiments, the system may determine a proposed diagnosis for the wearer, and cause the proposed diagnosis to be displayed via the client electronic device. The system may determine a proposed diagnosis for the wearer by sending the score to a diagnosis system, where the diagnosis system is configured to retrieve diagnosis information associated with a condition from a data store, where the diagnosis information comprises a known score associated with the condition, identify the condition as the proposed diagnosis in response to the score corresponding to the known score, and send an indication of the condition to the computing device.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device", "electronic device", or "computer" refers a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 4.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
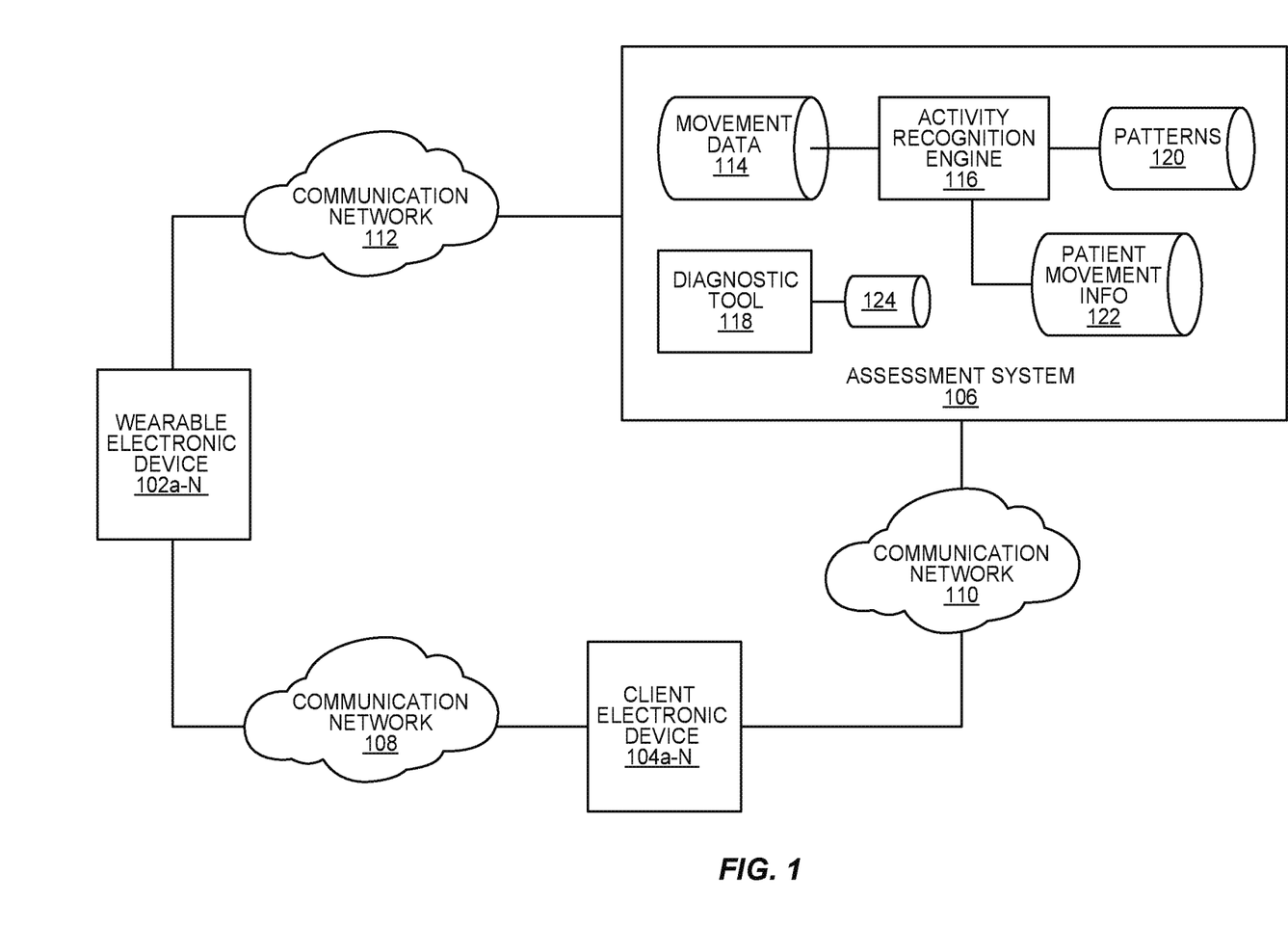
FIG. 1 illustrates an example spinal diagnostic system according to an embodiment.

FIG. 1 illustrates an example spinal evaluation system according to an embodiment. As illustrated by FIG. 1, the system 100 may include one or more wearable electronic devices 102a-N, one or more client electronic devices 104a-N, and an assessment system 106. The wearable electronic devices 102a-N may be in communication with a client electronic device 104a-N and/or the assessment system 106 via one or more communication networks 108, 112. Similarly, a client electronic device 104a-N may be in communication with the assessment system 106 via one or more communication networks 110. A communication network 108, 110, 112 may be a local area network (LAN), a wide area network (WAN), a mobile or cellular communication network, an extranet, an intranet, the Internet, a short range communication network and/or the like. Although FIG. 1 shows separate communication networks 108, 110, 112 it is to be understood that these networks, or some combination of these networks, may be implemented as a single communication network.

An assessment system 106 may include one or more electronic devices such as, for example, servers and/or one or more data stores. For instance, as shown in FIG. 1, an assessment system 106 may include a data store 114 for storing measured patient data that is received from one or more sensors such as, for example, movement data, electrical activity information, sound information, temperature information and/or the like. The data store 114 may store this data such that it is correlated to a particular patient.

An assessment system 106 may include an activity recognition system 116, which may be implemented using one or more electronic devices and/or data stores. An activity recognition system 116 may translate at least a portion of measured patient data to a particular activity performed by a wearer of a wearable electronic device as described in more detail below. An activity recognition system 116 may include or have access to a data store 120 that includes one or more patterns associated with one or more activities and/or a data store 122 that includes historical information about a wearer's patient data, such as movement data or patterns of movement.

In an embodiment, an assessment system 106 may include a diagnostic system 118. A diagnostic system 118 may be implemented using one or more electronic devices and/or data stores. A diagnostic system may analyze and compare measured patient data associated with a particular wearer of a wearable electronic device to data associated with various spinal or other back conditions or disorders to propose a possible diagnosis for a wearer, subject to clinician review and confirmation, as described in more detail below. As illustrated in FIG. 1, a diagnostic system may include or have access to a data store 124 that includes information associated with one or more spine or back conditions.

Figure 2:
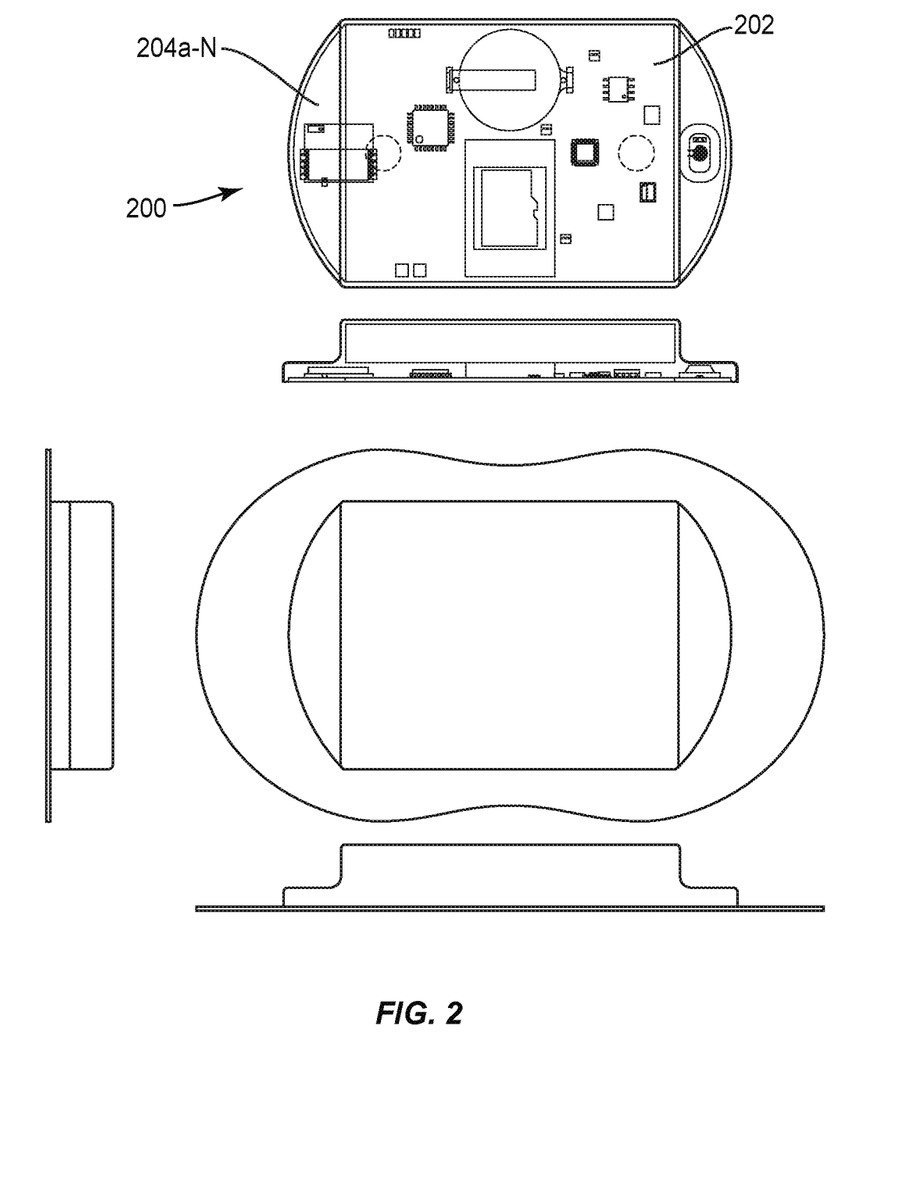
FIG. 2 illustrates an example wearable electronic device according to an embodiment.

FIG. 2 illustrates an example wearable electronic device 200 according to an embodiment. A wearable electronic device 200 may be configured to be worn by an individual across at least a portion of the individual's trunk, such as a portion of an individual's lower back, a portion of an individual's upper back, or anterior aspect of an individual's chest.

As illustrated by FIG. 2, a wearable electronic device 102a-N may include circuitry 202 and one or more sensors 204a-N. Example sensors 204a-N may include, without limitation, inertial measurement units (IMUs), electrocardiogram (ECG) sensors, electromyography (EMG) sensors, accelerometers, barometers, thermometers or other thermal sensors, microphones, photoplethysmography (PPG) and/or the like. In some embodiments, a wearable electronic device may be secured to a patient via one or more belts, straps or other fasteners. In other embodiments, a wearable electronic device may be a component of a wearable item, such as for example, a harness, a brace, a sleeve and/or the like, or may affix to the patient or wearer such as, for example, in the form of a subcutaneous implant or an external patch that may be adhesively or otherwise fixedly connected to the patient. In an embodiment, an adhesive used to fasten a wearable electronic device to a patient may be conductive to accommodate electrical signals flowing from a patient's skin to one or more sensors, such as an ECG integrated circuit.

In various embodiments, one or more sensors 204a-N may be configured to measure one or more characteristics of a wearer's movement or motion while the wearer is wearing the wearable electronic device. This movement or motion may be of a wearer's spinal axis, lower limbs and/or the like. For example, one or more sensors may measure rotation about an x, y, or z axis (e.g., pitch, roll and/or yaw). In various embodiments, an x-axis may be defined as the intersection of the mid-sagittal and axial planes. The y-axis may be defined as the intersection of the mid-coronal and axial planes. The z-axis may be defined as the intersection of the mid-sagittal and mid-coronal planes.

One or more sensors may measure angular velocity, gravity, pressure, acceleration, gyroscopic rotation and/or rotational orientation, direction in motion, heave, surge, sway, position and/or the like. Additional and/or alternate data may be used within the scope of this disclosure.

In certain embodiments, one or more sensors 204a-N may be configured to measure one or more anatomical conditions of a wearer. For example, a thermal sensor may measure a temperature of a patient's adjacent soft tissue. Similarly, a digital sensor, such as an ECG or PPG, may be used to measure a wearer's heartbeat. Additional and/or alternate data may be used within the scope of this disclosure.

One or more sensors 204a-N may be configured to measure electrical activity of local musculature of a patient. For instance, one or more sensors 204a-N may include ECGs or EMGs. In certain embodiments, one or more sensors 204a-N may be configured to measure sound information such as acoustical signals from nearby joints. For instance, one or more sensors 204a-N may include one or more microphones.

One or more sensors 204a-N, such as a pulse oximeter, may be configured to measure or detect blood volume changes in the microvascular tissue.

For purposes of this disclosure, "measured patient information" refers to information measured or otherwise obtained by a wearable electronic device such as, for example, movement data, anatomical conditions, electrical activity, sound information, blood volume changes and/or the like.

In various embodiments, a wearable electronic device 102a-N may include one or more integrated circuits, microchips or other memory devices. For instance, a wearable electronic device 102a-N may include a memory chip that may be removed from the wearable electronic device and inserted into another electronic device in order to transfer data stored on the memory chip. A wearable electronic device may also include firmware and/or a battery, including for example a thin film battery that may be encapsulated or may include a piezo-electronic powering.

In other embodiments, a wearable electronic device 102a-N may communicate with one or more other electronic devices such as, for example, a client electronic device 104a-N, via short range communication. For example, a wearable electronic device 102a-N may communicate with an electronic device using near field communication (NFC), radio frequency identification (RFID), Bluetooth and/or the like. A wearable electronic device and/or a client electronic device 104a-N may include a short range communication receiver and/or transmitter such as, for example, an RFID tag, a Bluetooth antenna, an NFC chip, ultrasound, and/or the like. The electronic device may further provide power, or additional power to the wearable electronic device through physical connection, induction, or by other such means.

A client electronic device 104a-N may be a smartphone, a tablet, a laptop, a computing device or other electronic device. For instance, a client electronic device 104a-N may be a smartphone or tablet associated with a patient. As another example, a client electronic device 104a-N may be a smartphone or tablet associated with a clinician, healthcare provider, healthcare entity and/or the like.

Figure 3:
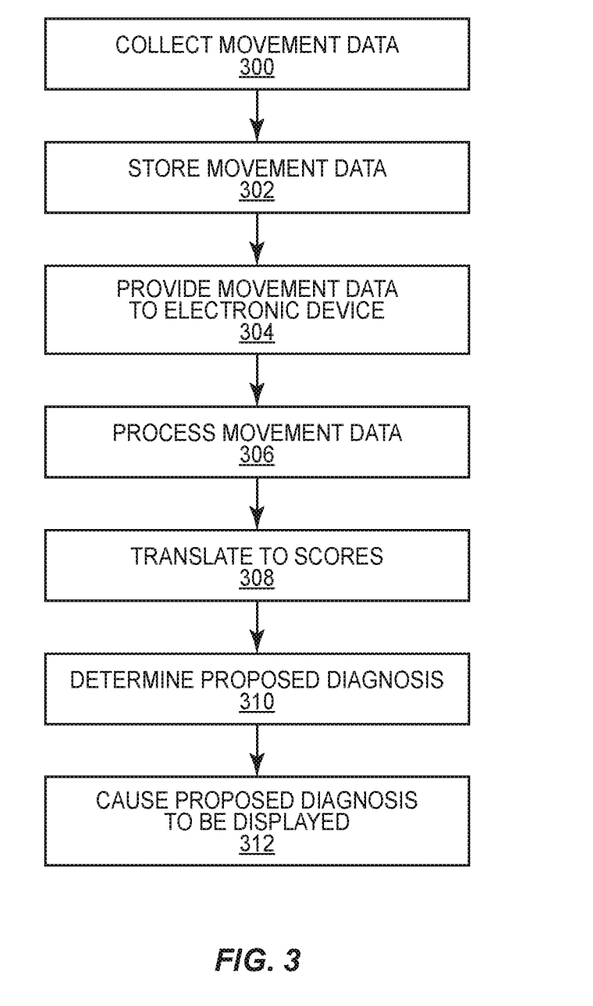
FIG. 3 illustrates an example method of evaluating patient data according to an embodiment.

FIG. 3 illustrates an example method of evaluating measured patient information according to an embodiment. As illustrated by FIG. 3, a wearable electronic device may collect 300 measured patient information during a certain time period. For example, an IMU may measure angular velocity and/or acceleration associated with a wearer's movement over a period of time. Similarly, a barometer may measure atmospheric pressure over a time period. In various embodiments, a sensor may continuously capture patient data. For example, a sensor may capture patient data substantially in real time. Alternatively, a sensor may capture patient data at certain times such as for example, at regular intervals.

An IMU may provide information pertaining to the motion of the person wearing the wearable electronic device given the IMU and its placement. The raw x/y/z measurements may, for example, provide only information about the movement of the sensor itself, which may be different from the movement of a wearer. For example, known approaches utilize motion sensors that are integrated into devices such as phones and watches, which move considerably different ways and ways that are independent of their wearers or carriers.

One or more data points of data may have one or more associated parameters such as an associated timestamp, an associated velocity value, an associated barometric pressure value, and associated acceleration value, a rotation value, an orientation value and/or the like.

In various embodiments, a patient may wear a wearable electronic device during the patient's day-to-day routine. For example, a patient may wear a wearable electronic device while the patient is home or otherwise outside of a clinical setting. The patient may wear a wearable electronic device for an extended period of time in order to obtain a large sample of data. This period of time may be hours, days, weeks, months and/or the like.

In other embodiments, a patient may wear a wearable electronic device for a limited period of time, such as, for example, in a clinical setting, during an evaluation with a clinician, and/or the like. In this situation, a patient may be asked to perform one or more movements, activities or protocols to gather information about the patient's movement. For instance, a clinician may ask a patient to sit, stand, walk, bend over, lay down or perform other activities while wearing a wearable electronic device.

In various embodiments, a wearable electronic device may notify a wearer or another person, such as a health care provider, if one or more measurements of patient data are outside of an acceptable range. For instance, a wearable electronic device may include or be in communication with a data store which may store an acceptable range of measurements. The acceptable range of measurements may be a customized range particular to a wearer, or it may be a generalized range of acceptable measurements across patients. For instance, a sensor may measure the rotation about an axis. If the measured rotation is outside of an acceptable range of values (e.g., the wearer is rotating too much), then the wearable electronic device may cause a notification to be displayed at a client electronic device notifying a user of the client electronic device that the measurement is outside of acceptable ranges. Additional and/or alternate ranges and/or measurements may be used within the scope of this disclosure.

Referring back to FIG. 3, in some embodiments, a wearable electronic device may perform one or more pre-processing operations on at least a portion of collected patient data. For example, a wearable electronic device may filter data or format data to be in a consistent form or format.

A wearable electronic device may store 302 the collected patient data in one or more data stores. In various embodiments, a data store may be associated with a sensor so that movement data collected by the sensor is stored in the corresponding data store. Alternatively, patient data collected by one sensor may be stored in one or more data stores along with movement data collected by one or more other sensors.

As illustrated by FIG. 3, at least a portion of the stored patient data may be provided to 304 an electronic device. In an embodiment, patient data may be provided to an electronic device by removing a memory chip or other data store from a wearable device, and connecting it to an electronic device. Alternatively, a wearable electronic device may transmit at least a portion of collected patient data to an electronic device via one or more communication networks. In some embodiments, a wearable electronic device may transmit patient data to an electronic device at certain times or intervals. In other embodiments, a wearable electronic device may transmit patient data to an electronic device in response to receiving a request from the electronic device.

One or more electronic devices, such as ones associated with an assessment engine or activity recognition system, may process 306 at least a portion of the patient data. In various embodiments, an electronic device may process 306 movement data that is included in patient data to classify at least a portion of the movement data into one or more activity categories. An activity category refers to an activity that a wearer may be performing when at least a portion of the patient data is collected. Example activity categories include, without limitation, sleeping, walking, driving, traveling, sitting, standing and/or the like.

In various embodiments, an electronic device may classify movement data into an initial grouping. The initial grouping may be associated with a wearer's posture. As such, an initial grouping may be associated with two or more activity categories. For example, activity categories may be associated with similar types of postures. As such, movement data may be first categorized into an initial grouping based on characteristics of the movement data such as, for example, rotational position about one or more anatomic axes.

An electronic device may use a machine learning technique to classify movement data into an initial grouping. For instance, an electronic device may use a logistic regression trained on certain postures. Logistic regression operates on a purely binary bases, but it can be extended to a multi-class classification task using multinomial logistic regression or one-vs-rest voting. Multinomial logistic regression generalizes the approach to that it can produce more than one output classification. For example, instead of true or false, the possible outputs of logistic regression, multinomial logistic regression may label three posture states directly.

One-vs-rest (or one-vs-all) is a process where individual classifiers are trained in a binary way to identify data as "X" or "everything but X." In this case, each possible posture may be associated with its own classifier (e.g., a standing classifier, a sitting classifier and a recumbent classifier). Data may be passed through the classifiers associated with each possible posture, and the result with the highest probability value may be assumed to be the correct posture.

An electronic device may further classify the movement data for each initial grouping as a specific activity category of the initial grouping. For instance, an electronic device may categorize movement data that has been classified into the initial grouping "Activity 1/Activity 2" as either activity category Activity or activity category Activity 2.

An electronic device may classify movement data into an initial grouping and/or an activity category based on one or more parameter values of the movement data. For instance, movement data indicating that the wearable electronic device is positioned in an upright manner on a wearer's back may be and subject to a barometric pressure in a certain range may be classified in an initial grouping "Activity 1/Activity2." However, such movement data may be classified in the Activity 2 activity category if the movement data is associated with a velocity that is within a certain range or that exceeds a certain value.

As another example, movement data indicating that a wearable electronic device is experiencing a force within a certain range may be classified into an initial grouping "Activity 3/Activity 4." However, such movement data may be classified in the Activity 3 activity category if the movement data is associated with a velocity that is within a certain range or that exceeds a certain value since a wearer would traditionally not experience this velocity during sleep.

In various embodiments, an electronic device may use pattern matching to classify movement data. For instance an electronic device may store or otherwise have access to one or more data patterns that are indicative of movement that corresponds to an initial grouping and/or an activity category. For example, movement data associated with walking may have a velocity parameter value that is within a certain range of values. This pattern may be stored in a pattern data store. When classifying movement data, an electronic device may compare at least a portion of the movement data with one or more patterns to determine one or more similarities. For instance, if velocity parameter values associated with a portion of movement data are similar to the example "walking" pattern described above, an electronic device may classify this portion of movement data as "walking."

In some embodiments, one or more patterns may be trained based on specific behaviors or movements of an individual wearer. An electronic device may utilize a machine learning method which may compare at least a portion of movement data against a trained data set to determine a probability that the movement data corresponds to a pattern associated with an activity category. For instance, a particular wearer may consistently walk with a velocity that is within a certain range. As another example, a wearer may consistently walk with gait that favors the wearer's fight side. As more movement data is collected for a wearer, one or more patterns may be trained to recognize that certain behaviors are specific to a wearer's movement and are not an indication of pain or other consequences of a back condition being experienced by the wearer.

Referring back to FIG. 3, an electronic device may translate 308 at least a portion of the classified movement data and/or other of the patient data into one or more scores. In various embodiments, the one or more scores may correspond to one or more questions from the ODI. For example, the ODI may ask a patient evaluate how the patient's pain has impacted his or her ability to walk. An electronic device may analyze one or more parameters of the movement data that has been classified as "walking" to generate a score associated with the question. For example, an electronic device may analyze a forward velocity associated with the movement data to determine how quickly a wearer was moving. As another example, an electronic device may analyze pitch (forward to backward motion) and/or roll (right to left movement), to determine how steady the wearer was walking.

Referring back to FIG. 3, in certain embodiments, an electronic device may determine 310 a proposed diagnosis for a wearer. For instance, an activity recognition system may send one or more of the scores to a diagnosis system. The diagnosis system may receive the scores and may compare the scores to diagnosis information associated with various conditions, such as, for example, cervical myelopathy and symptomatic lumbar spinal stenosis. For instance, a diagnosis system may store information associated with different conditions in one or more data stores. This information may include a score or a range of scores for various movement-related aspects of the condition. If the received scores are similar to the scores associated with a condition, a diagnosis system may determine that the condition is a proposed diagnosis for the wearer.

For example, a neurogenic claudication associated with spinal stenosis may be characterized by progressive lumbar flexion and decrease walking speed with increased ambulation. In contrast, lumbar muscular dysfunction (spasm) may be characterized by improved posture and walking speed with increased ambulation In various embodiments, an assessment system may cause a proposed diagnosis to be displayed 312 on one or more client electronic devices. For instance, an assessment system may cause a proposed diagnosis to be displayed on a tablet associated with the wearer's clinician. In another embodiment, an assessment system may cause a proposed diagnosis to be displayed on a wearer's smartphone device. A clinician may use the proposed diagnosis to confirm a diagnosis for a wearer or make other treatment recommendations for the wearer.

Figure 4:
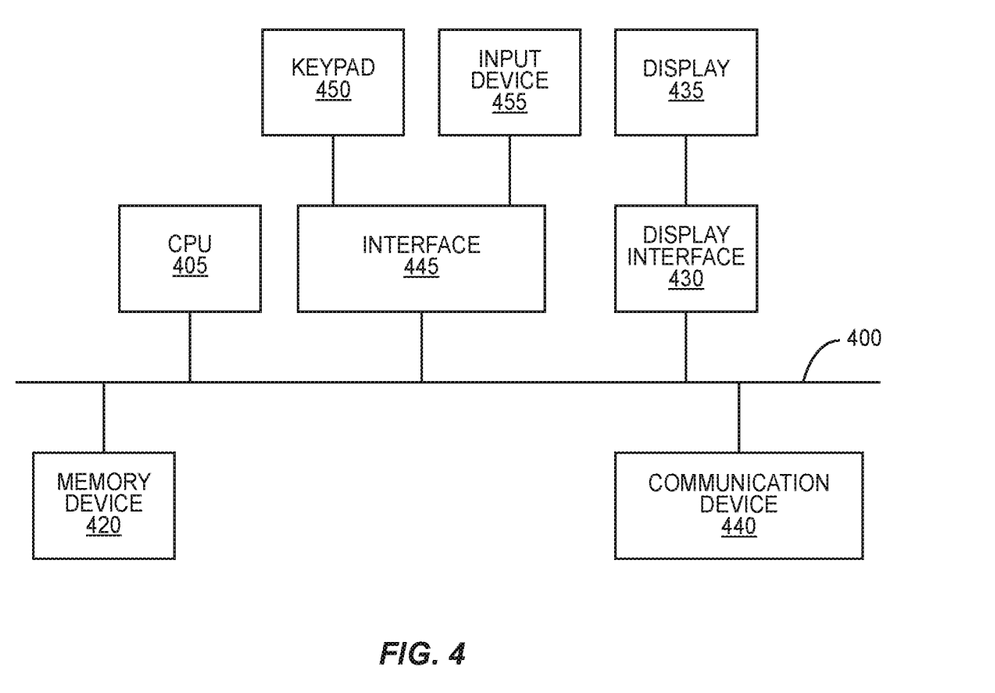
FIG. 4 depicts a block diagram of an example of internal hardware that may be used to contain or implement program instructions according to an embodiment.

FIG. 4 illustrates example hardware that may be used to contain or implement program instructions. A bus 400 serves as the main information highway interconnecting the other illustrated components of the hardware. CPU 405 is the central processing unit of the system, performing calculations and logic operations required to execute a program. CPU 405, alone or in conjunction with one or more of the other elements disclosed in FIG. 4, is an example of a processor as such term is used within this disclosure. Read only memory (ROM) and random access memory (RAM) constitute examples of non-transitory computer-readable storage media 420, memory devices or data stores as such terms are used within this disclosure.

Program instructions, software or interactive modules for providing the interface and performing any querying or analysis associated with one or more data sets may be stored in the memory device 420. Optionally, the program instructions may be stored on a tangible, non-transitory computer-readable medium such as a compact disk, a digital disk, flash memory, a memory card, a USB drive, an optical disc storage medium and/or other recording medium.

An optional display interface 430 may permit information from the bus 400 to be displayed on the display 435 in audio, visual, graphic or alphanumeric format. Communication with external devices may occur using various communication ports 640. A communication port 440 may be attached to a communications network, such as the Internet or an intranet.

The hardware may also include an interface 445 which allows for receipt of data from input devices such as a keypad 450 or other input device 455 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also that various presently unforeseen or unanticipated alternatives, modifications, variations or improvements therein may be subsequently made by those skilled in the art which are also intended to be encompassed by the following claims.

What is claimed is:

1. A system for assessing a spinal disorder, the system comprising:
a wearable electronic device comprising:
one or more sensors configured to obtain patient data associated with a wearer of the wearable electronic device, and
a short-range communication transmitter,
wherein the wearable electronic device is configured to be positioned on a portion of a lower back of a wearer,
wherein the one or more sensors comprises an inertial measurement unit that measures movement data of the wearer over a period of time, wherein the movement data comprises an angular velocity and an acceleration of movement of the lower back of the wearer over the period of time,
an assessment system comprising:
a computing device in communication with the wearable electronic device, wherein the computing device comprises a short-range communication receiver, and
a computer-readable storage medium comprising one or more programming instructions that, when executed, cause the computing device to:
receive patient data via the short-range communication receiver from the short-range communication transmitter over a period of time, wherein the patient data comprises the movement data,
train a plurality of classifiers, wherein each classifier corresponds to one of a plurality of postures, wherein each posture is associated with a plurality of activity categories that correspond to different types of movement,
classify at least a portion of the movement data into an initial grouping by:
applying each of the classifiers to the at least a portion of the movement data, and
selecting the posture that corresponds to the classifier that yields a highest probability value as the initial grouping,
further classify the at least a portion of the movement data into one of the plurality of activity categories,
generate a score corresponding to the at least a portion of the movement data based on the activity category to which the movement data is classified, and
cause the score to be displayed via a client electronic device.

2. The system of claim 1, wherein the one or more sensors comprise one or more of the following:
an electrocardiogram sensor;
an altimeter;
a barometer;
a photoplethysmogram;
a thermometer; or
a microphone.

3. The system of claim 1, wherein the patient data comprises measurements related to one or more of the following:
electrical activity information;
sound information; or
temperature information.

4. The system of claim 1, wherein the one or more programming instructions that, when executed, cause the computing device to classify at least a portion of the movement data into an initial grouping comprise one or more programming instructions that, when executed, cause the computing device to compare one or more parameter values of the movement data to one or more parameters associated with one or more possible initial groupings.

5. The system of claim 1, wherein the one or more programming instructions that, when executed, cause the computing device to classify the at least a portion of the movement data into one of the plurality of activity categories comprise one or more programming instructions that, when executed, cause the computing device to compare the at least a portion of the movement data to a trained data set to determine a probability that the at least a portion of the movement data corresponds to a pattern associated with one of the plurality of activity categories.

6. The system of claim 5, wherein the computer-readable storage medium further comprises one or more programming instructions that, when executed, cause the computing device to use the at least a portion of the movement data to train or reinforce the trained data set as to movement specific to the wearer.

7. The system of claim 1, wherein the plurality of activity categories comprise one or more of the following:
sleeping;
driving;
sitting;
standing; or
walking.

8. The system of claim 1, wherein the computer-readable storage medium further comprises one or more programming instructions that, when executed, cause the computing device to: determine a proposed diagnosis for the wearer, and
cause the proposed diagnosis to be displayed via the client electronic device.

9. The system of claim 8, wherein the one or more programming instructions that, when executed, cause the computing device to determine a proposed diagnosis for the wearer comprise one or more programming instructions that, when executed, cause the computing device to:
send the score to a diagnosis system,
wherein the diagnosis system is configured to:
retrieve diagnosis information associated with a condition from a data store,
wherein the diagnosis information comprises a known score associated with the condition,
identify the condition as the proposed diagnosis in response to the score corresponding to the known score, and
send an indication of the condition to the computing device.

10. A method of assessing a spinal disorder, the method comprising:
by a computing device of an assessment system:
receiving, by a short-range communication receiver, patient data from one or more sensors of a wearable electronic device that is positioned on a portion of a lower back of a wearer, wherein the patient data comprises movement data associated with movement of the lower back of the wearer, wherein the one or more sensors include an inertial measurement unit that measures movement data of the wearer over a period of time, wherein the movement data comprises an angular velocity and an acceleration of movement of the lower back of the wearer over the period of time,
training a plurality of classifiers, wherein each classifier corresponds to one of a plurality of postures, wherein each posture is associated with a plurality of activity categories that correspond to different types of movement,
classifying at least a portion of the movement data into an initial grouping by:
applying each of the classifiers to the at least a portion of the movement data,
and
selecting the posture that corresponds to the classifier that yields a highest probability value as the initial grouping,
further classifying, the at least a portion of the movement data into one of the plurality of activity categories,
generating a score corresponding to the at least a portion of the movement data based on the activity category to which the movement data is classified, and
causing the score to be displayed via a client electronic device.

11. The method of claim 10, wherein the one or more sensors comprise one or more of the following:
an electrocardiogram sensor;
an altimeter;
a barometer;
a photoplethysmogram;
a thermometer; or
a microphone.

12. The method of claim 10, wherein the patient data comprises measurements related to one or more of the following:
electrical activity information;
sound information; or
temperature information.

13. The method of claim 10, wherein classifying at least a portion of the movement data into an initial grouping comprises comparing one or more parameter values of the movement data to one or more parameters associated with one or more possible initial groupings.

14. The method of claim 10, wherein classifying the at least a portion of the movement data into one of the plurality of activity categories comprises comparing the at least a portion of the movement data to a trained data set to determine a probability that the at least a portion of the movement data corresponds to a pattern associated with one of the plurality of activity categories.

15. The method of claim 14, further comprising using the at least a portion of the movement data to train or reinforce the trained data set as to movement specific to the wearer.

16. The method of claim 10, wherein the plurality of activity categories comprise one or more of the following:
sleeping;
driving;
sitting;
standing; or
walking.

17. The method of claim 10, further comprising:
determining a proposed diagnosis for the wearer, and
causing the proposed diagnosis to be displayed via the client electronic device.

18. The method of claim 17, wherein determining a proposed diagnosis for the wearer comprises:
sending the score to a diagnosis system,
wherein the diagnosis system is configured to:
retrieve diagnosis information associated with a condition from a data store, wherein the diagnosis information comprises a known score associated with the condition,
identify the condition as the proposed diagnosis in response to the score corresponding to the known score, and
send an indication of the condition to the computing device.

* * * * *

UNITED STATES PATENT AND TRADEMARK OFFICE
CERTIFICATE OF CORRECTION

| | | |
|---|---|---|
| PATENT NO. | : 11,278,238 B2 | |
| APPLICATION NO. | : 16/132094 | |
| DATED | : March 22, 2022 | |
| INVENTOR(S) | : Nicholas M. Benson et al. | |

It is certified that error appears in the above-identified patent and that said Letters Patent is hereby corrected as shown below:

On the Title Page

Item (72) Inventors please add inventor: -- Dr. Kevin T. Foley, Germantown, TN (US) --

Signed and Sealed this
Ninth Day of July, 2024

Katherine Kelly Vidal
*Director of the United States Patent and Trademark Office*